United States Patent [19]

Schammel

[11] Patent Number: 4,992,579

[45] Date of Patent: Feb. 12, 1991

[54] PROCESS FOR THE PRODUCTION OF TRIMELLITIC ACID

[75] Inventor: Wayne P. Schammel, Naperville, Ill.

[73] Assignee: Amoco Corporation, Chicago, Ill.

[21] Appl. No.: 451,606

[22] Filed: Dec. 18, 1989

[51] Int. Cl.$^5$ .......................................... C07C 51/215
[52] U.S. Cl. .................................. 562/413; 562/414; 562/416; 562/417; 562/480; 502/304
[58] Field of Search ............... 562/413, 414, 480, 416, 562/417; 502/304

[56] References Cited

U.S. PATENT DOCUMENTS 3,491,144  1/1970  Ember et al. ........................ 562/413
4,719,311  1/1988  Partenheimer ...................... 562/413
4,835,308  5/1989  Sakakibara et al. ................ 562/413

Primary Examiner—Werren B. Lone
Assistant Examiner—Vera C. Clarks
Attorney, Agent, or Firm—Gunar J. Blumberg; William H. Magidson; Ralph C. Medhurst

[57] ABSTRACT

A process for the manufacture of trimelitic acid from pseudocumene is disclosed. The pseudocumene is oxidized in the presence of a cerium, cobalt, manganese, and optionally zirconium, bromine catalyst wherein all of the cerium is added in the second stage of the oxidation, and wherein most of the bromine is also added during the second oxidation stage. Trimellitic acid is useful in the manufacture of polyester and polyamide-imides.

26 Claims, No Drawings

PROCESS FOR THE PRODUCTION OF TRIMELLITIC ACID

BACKGROUND OF THE INVENTION

The field of this invention relates to the liquid-phase oxidation of pseudocumene (PSC). In one aspect, this invention relates to conducting the initial part of the reaction in a semi-continuous or batch mode followed by a batch tail-out wherein most of the bromine promoter and cerium in the plus three valence is added in the batch tail-out stage, thus reducing the contact time of the polycarboxylic acid moieties with cobalt-manganese-bromine or zirconium-cobalt-manganese-bromine catalysts and improving the yield of trimellitic acid (TMLA) from PSC.

The bromine-polyvalent metal catalysts in acetic acid solvent have been in commercial use in many countries for the manufacture of terephthalic acid from p-xylene for many years. However, in the absence of acetic acid solvent, the best yield of a single phthalic acid (e.g., terephthalic acid) on a once-through basis of the xylene amounted to about 20 weight percent (12.8 mole %), according to U.S. Pat. No. 2,833,816. According to U.S. Pat. No. 3,920,735, the Mn-Br and Co-Mn-Br catalyst systems are improved by the addition of zirconium. However, not mentioned, but illustrated in Tables I, II and IV in U.S. Pat. No. 3,920,735, is the fact that, when part of the zirconium is added, combustion of the feedstock to carbon dioxide increases. The use of cerium has been disclosed in the U.S. Pat. No. 3,491,144 however, in that reference cerium is not added to the batch tail-out part of the reaction in the plus three valence state wherein the amount of bromine added is reduced.

DESCRIPTION

My novel invention is a process for the oxidation of pseudocumene PSC with molecular oxygen to TMLA under liquid-phase conditions in the presence of a cobalt-manganese-cerium-bromine catalyst or a cerium zirconium-cobalt-manganese-bromine catalyst wherein the atomic ratio of cerium to cobalt is in a range from 1 to about 2 to about 1 to about 25, which process comprises conducting a semi-continuous oxidation of the PSC so that the concentration of the polycarboxylic acids is very low, permitting only partial oxidation of the PSC, thus avoiding the poisoning of the catalyst and completing the reaction in a non-continuous process at a temperature of about 120° C. to about 175° C. to about 150° C. to about 275° C. wherein most of the bromine and all of the cerium catalyst is added in the tail-out part of the reaction.

In a preferred embodiment my process comprises the oxidation of PSC with molecular oxygen to TMLA under liquid-phase conditions in the presence of a zirconium-cobalt-manganese-cerium-bromine catalyst or a cobalt-manganese-cerium-bromine catalyst, wherein the atomic ratio of cerium to cobalt is about 1:2 to about 1:25 at a temperature in the range of about 100° C. to about 200° C., conducted using a semi-continuous or batch oxidation of the pseudocumene so that the amount of bromine in the first stage added is about 0 to about 35 percent of the total bromine added and the remainder is added in the second stage which is calculated to provide the total bromine-to-metals atomic ratio of about 0.3 to about 1.5, preferably in the range of about 0.4 to about 0.7. The concentration of pseudocumene is kept low so that only one methyl group on the average on the benzene ring is converted to a carboxylic acid group, thus avoiding the poisoning of the catalyst and completing the reaction in a non-continuous process at a temperature of about 120° C. to about 175° C. to about 150° C. to about 250° C.

In another preferred embodiment, my process for the oxidation of PSC with molecular oxygen to TMLA under liquid-phase conditions in the presence of a cerium-zirconium-cobalt-manganese-bromine catalyst wherein the atomic ratio of total zirconium to cobalt is about 1:15 to about 1:45, and the ratio of cerium to cobalt is about 1:2 to about 1:25, at a temperature in the range of about 100° C. to about 275° C. comprises conducting a semi-continuous oxidation of PSC so that only about one to about two of the methyl groups on a benzene ring are converted to carboxylic acid groups, thus avoiding the poisoning of the catalyst and completing the reaction in a non-continuous process at a temperature of about 120° C. to about 175° C. to about 150° C. to about 250° C. Cerium is added only in the non-continuous process stage. For each gram mole of PSC, the concentration of catalyst metals, i.e., cerium, zirconium and cobalt plus manganese, used is in the range of about 3 to about 10 milligram atoms total, and the concentration of bromine used is in a range of about 1.4 to about 10 milligram atoms total per gram mole of PSC.

Zirconium can be added to the reaction in any form soluble in the PSC being oxidized or in acetic acid when it is being used as reaction solvent. For example, zirconium octanoate or naphthanate can be used with manganese and cobalt octanoates or naphthanics for oxidation of PSC in the absence of reaction solvent and each of Zr, Mn, and Co can be conveniently used as its acetate when PSC is oxidized in the presence of acetic acid solvent. Zirconium is available on a commercial basis as a solution of $ZrO_2$ in acetic acid and, as such, is ideally suited for liquid-phase oxidations using acetic acid as reaction solvent. The cerium is added in the tail-out reaction having a valence of plus three. Suitable cerium compounds must be soluble in the tail-out solution and they include cerium carbonate and cerium acetate.

The source of molecular oxygen for the enhanced oxidation of this invention can vary in $O_2$ content from that of air to oxygen gas. Air is the preferred source of molecular oxygen for oxidations conducted at temperatures of 120° C. and above up to 275° C. For oxidation conducted with molecular oxygen, the preferred temperatures are in the range of 100° C. to 200° C. The minimum pressure for such oxidations is that pressure which will maintain a substantial liquid phase of 70-80 percent of the reaction medium, either neat PSC, or PSC and 70-80 percent of the acetic acid. The acetic acid solvent, when used, can amount to 1-10 parts on a weight basis per part of the PSC. The PSC and/or acetic acid not in the liquid phase because of vaporization by heat of reaction is advantageously condensed and the condensate returned to the oxidation as a means for removing heat and thereby temperature controlling the exothermic oxidation reaction. Such vaporization of PSC reactant and/or acetic acid solvent is also accompanied by vaporization of lower boiling by-product water. When it is desired to take advantage of the benefits of withdrawing acetic acid and water of reaction from the liquid-phase oxidation, as will be hereinafter demonstrated, condensate is not returned to the oxidation.

My reaction, as applied to PSC, is very difficult and has only been practiced as a batch process in the prior art for the oxidation of PSC because the reaction product, TMLA, is poison for the catalyst. Batch reactions are successful because high concentrations of the product acid occur only near the end of the oxidation, while in continuous oxidations, the product concentration is at a constant high level. Batch oxidations, however, have disadvantages because the concentration of the hydrocarbon near the beginning of the oxidation is high and its rate of oxidation difficult to control. This leads to a low concentration of dissolved oxygen and increased amounts of hydrocarbon radical reactions producing dimeric, high-boiling side products which reduce the yield. Thermally induced destruction of methyl groups of PSC is also known to occur, leading to xylene which eventually become oxidized to dicarboxylic acid groups, thus leading to yield loss. In my novel process, I bypass the difficulties of both batch and continuous oxidations. In this two-step process, I first conduct a semi-continuous oxidation in a manner so that (1) only about one to about two methyl groups on a benzene ring become oxidized to avoid catalyst poisoning, (2) the hydrocarbon concentration is kept low to eliminate much of the radical dimerization reactions, and (3) the temperature is maintained sufficiently low to minimize the destruction of methyl groups. Then, in the second step, I batch oxidize in the presence of cerium and bromine the resultant material from the semi-continuous oxidation so that high concentrations of poisonous product acids occur only near the end of the oxidation.

I have established that my novel process results in predominantly dimethylbenzoic acids under the conditions used in my semi-continuous step. The semi-continuous part of the oxidation is carried out suitably during the first 30 minutes of the oxidation.

The semi-continuous part of the oxidation is conducted so that the concentration of polycarboxylic acids is low, usually about 1–5 mole percent, thus preventing premature catalyst deactivation. Thus, the theoretical oxygen uptake is somewhere between 1 and 2.5 moles $O_2$/mole hydrocarbon, with 1.5–2 moles being preferred. Because of side reactions, the actual oxygen uptake may be slightly higher. Also, the semi-continuous oxidation is run at a low enough temperature, usually about 120° C. to about 200° C., to allow maintenance of an oxygen concentration above 0.5 percent in the vent gas, with 2–8 percent being preferred. After all the hydrocarbon has been pumped in, the oxidation is finished in a non-continuous process. In the non-continuous batchwise step, the temperature of reaction is increased from a temperature in the range of about 120° C. to about 175° C., to a final temperature in the range of about 150° C. to about 250° C. to compensate for the decreasing reaction rate. In this step, cerium, bromine, manganese, zirconium, and optionally cobalt, alone or in any combination, are added.

In the batchwise oxidation of PSC, the exothermic heat of reaction vaporizes some of the liquid solvent which is carried out by the reactor by the process air. The solvent is condensed and returned to the reactor as reflux. This liquid reflux is reheated toward the end of the reaction cycle to ensure temperatures high enough to bring the oxidation to completion. After reaction, the reactor contents are depressurized and TMLA is crystallized out to form a 50–60 percent solids slurry (close to the maximum solids concentration that is pumpable). The solids are filtered out and further processed into final product. The filtrate is disposed of and, therefore, represents a significant yield loss.

Under the conditions embodied by my novel process, the solvent condensed out of the reactor vent gas is withdrawn and not returned as reflux to the reactor. Solvent withdrawal maintains reactor temperatures high enough to compete the reaction thereby saving energy due to the elimination of reflux reheating. The withdrawn solvent is rich in water as opposed to a saturated lower aliphatic acid, i.e., acetic acid. Therefore, since TMLA is ten times more soluble in water than in acetic acid, with water-rich solvent withdrawal the crystallizer effluent is suitably thickened to 70 percent solids instead of 60 percent, thereby recovering more TMLA and reducing filtrate losses. In practice, a slurry containing more than 70 percent solids is difficult to pump. To ease operating problems, enough filtrate, which is saturated with TMLA is pumped to the crystallization section to provide pumpability while maintaining an overall increase in yield. Usually, about 20 to about 80 percent of the total filtrate is pumped to the crystallization section.

An alternate suitable embodiment of the present invention comprises the withdrawal of the condensed solvent, acetic acid and water of reaction during the last 5 to about 20 percent of the oxidation reaction period using acetic acid reaction medium in the weight ratio to PSC of about 1.0:1.0 to about 2.5:1.0. The metal oxidation catalyst components are cerium, cobalt, zirconium and manganese or cerium, cobalt and manganese. Total metal concentration for each gram mole of PSC is in the range of about 3 to about 10, preferably about 5 to about 8 milligram atoms in combination with a source of bromine, providing a bromine concentration of about 1.4 to about 10, preferably about 3 to about 7 milligram atoms per gram mole of PSC. The manganese component of the catalyst is at least 8 weight percent, preferably in the range of about 25 to about 40 weight percent based on the total weight of catalyst metals. The cerium content of the total metals used is in the range of about 9 to about 30, preferably about 15 to about 22 weight percent. The zirconium content of the total metals used is in the range of about 2 to about 5, preferably about 3 to about 4 by weight percent of the total metals. The cobalt component of the catalyst is in the range of about 30 to about 70 weight percent of the total metals.

Another alternate and suitable mode of conduct for the catalytic liquid-phase air oxidation of PSC to TMLA is staged addition of the cerium and bromine component. This improved mode of conduct provides a shorter overall reaction cycle, reduces metals corrosion and contamination of desired crude product while improving the high yields of the desired acid and low production of methylphthalic acids' and formylphthalic acids' impurities which are features of the prior art. This improved staging of the cerium and bromine component permits the use of lower metals and acetic acid-to-PCS ratio, and provides crude TMLA products of lower metals and bromine-containing impurities which can be more conveniently removed from crude TMLA as the case may be. Other advantages from this improved mode of conduct for cerium and bromine staging will be apparent from the disclosure which follows.

It is particularly desirable to oxidize PSC as completely as possible to TMLA not only to obtain high yields of the acid product in the oxidation effluent, but also to provide potential of recovery of crude TMLA product with low partial oxidation impurities without extensive oxidation of acetic acid. Low impurity formation is a goal also desirable because TMLA is rather soluble in acetic acid and the methylphthalic acids' and formylphthalic acids' impurities appear to enhance the solubilities of TMLA and leading to contamination of the product precipitated from the oxidation effluent, especially a concentrate thereof. Thus, the partial oxidation products in the oxidation effluent have a limiting effect on TMLA precipitations by crystallization from said effluent, making necessary additional processing steps to effect recovery of the remaining TMLA solutes in the mother liquor after separation from first crop product. Also, the presence of the impurities requires special processing of the total crude TMLA to obtain it in commercially acceptable quality as its intramolecular anhydride.

The present inventive staged addition of cerium and bromine for the catalytic liquid-phase air oxidation of PSC to TMLA is conducted using acetic acid reaction medium in the weight ratio of PSC of about 1.0:1.0 to about 2.5:1.0. The metal oxidation catalyst components are cerium, cobalt, zirconium and manganese or cerium, cobalt and manganese. Total metal concentration based on a gram mole of PSC is in the range of about 3 to about 10, preferably about 5 to about 8, milligram atoms in combination with a source of bromine, providing a bromine concentration of about 1.4 to about 10, preferably about 3 to about 7 milligram atoms per gram mole of PSC. The manganese component of the catalyst is at least 8 weight percent, preferably in the range of about 25 to about 40 weight percent based on the total weight of catalyst metals. The zirconium content of the total metals used is in the range of about 2 to about 5, preferably about 3 to about 4, percent by weight of total metals. The cobalt component of the catalyst is in the range of about 30 to about 70 weight percent of the total metals. The cerium content of the total metals used is in the range of about 9 to about 30, preferably about 15 to about 22, percent by weight of total metals.

When the oxidation of PSC is conducted batchwise, all of the PSC and most (90–99 percent) of the acetic acid and initial amount of catalyst components except cerium and bromine are charged at or near oxidation initiation temperature, preferably at about 120° C. to about 165° C., and at a pressure to maintain liquid-phase conditions. Then, pressurized air is injected into the reaction mixture, and the reaction temperature is permitted to increase by heat evolved by the oxidation reaction to about 175° C. to about 225° C.

The total bromine added can be from a single source of bromine, for example, ionic bromine sources (HBr, NaBr, NH$_4$Br and the like) or from a combined form of bromine, for example, organic bromides such as benzyl bromide, tetrabromoethane and others.

My novel process relates to the liquid-phase oxidation of PSC to TMLA using cerium, cobalt, manganese and/or other variable-valence metals plus bromine, and when desired, zirconium. A useful catalyst for my process is a cerium-zirconium-cobalt-manganese-bromine catalyst wherein the molecular ratio of cerium to cobalt is about 1:2 to about 1:25, and the molecular ratio of zirconium to cobalt is about 1 to about 10 to about 1 to about 100 and the oxidation is conducted at a temperature in the range of about 100° C. to about 220° C., which process comprises conducting an oxidation of the pseudocumene so that the first stage is a continuous or alternatively is a batch stage oxidation of PSC so that the concentration of bromine in the first stage is 0 to about 0.5 mole per mole of metals while all the remaining bromine is added during the second stage. The total amount of bromine added is about 30 to about 180 weight percent of the total metal catalysts present. The reaction is completed in a non-continuous process at a temperature of about 140° C. to about 250° C. and, if desired, the solvent and water of reaction is withdrawn during the last 5 to about 20 percent of the period of the reaction, usually during the last 5 to 20 minutes of the reaction, thus leaving higher TMLA of PA concentrations in the liquid-phase oxidation reactor effluent. In this process, the cerium is added during the second stage.

In an advantageous embodiment of my process for the oxidation of PSC with molecular oxygen to TMLA under liquid-phase conditions in the presence of a cerium-zirconium-cobalt-manganese-bromine catalyst, the atomic ratio of zirconium to cobalt is about 1:10 to about 1:100. The atomic ratio of cerium to cobalt is about 1:2 to about 1:25, and the initial temperature is in the range of about 100° C. to about 220° C. This process comprises conducting an oxidation of the PSC so that in the first stage the amount of bromine added is below about 35 weight percent of the total bromine to be added, and the cerium is added during the second stage. Also, this process comprises permitting only partial oxidation of the PSC, thus avoiding the poisoning of the catalyst and completing the reaction in a non-continuous process at a temperature of about 140° C. to about 175° C. to about 150° C. to about 250° C. During the last 5 to about 20 percent of the reaction time, the solvent and water of reaction are withdrawn leaving about 60 to about 75 weight percent solids in the crystallizer effluent.

In a suitable embodiment of my process for the oxidation of PSC with molecular oxygen to TMLA under liquid-phase conditions in the presence of a cerium-zirconium-cobalt-manganese-bromine catalyst, the molecular ratio of zirconium to cobalt is about 1:10 to about 1:100, and the molecular ratio of cerium to cobalt is about 1:2 to about 1:25. This process comprises conducting a semi-continuous or batch oxidation of the PSC so that in the first stage the amount of bromine added is below 20 weight percent of the total bromine to be added. The cerium is added during the second stage. The reaction is completed in a non-continuous process at a temperature of about 120° C. to about 175° C. to about 150° C. to about 250° C.

In an alternate embodiment, my process for the oxidation of PSC with molecular oxygen to TMLA under liquid-phase conditions is conducted in the presence of a cerium-cobalt-manganese-bromine catalyst. This process comprises conducting a semi-continuous or batch oxidation of pseudocumene so that in the first stage no bromine is added or not more than 35 percent of the total bromine is added. The reaction is completed with the addition of cerium in a non-continuous process at a temperature of about 120° C. to about 175° C. to about 150° C. to about 250° C.

It has now been discovered that my novel, staged cerium and bromine addition process can be further improved by running a semi-continuous oxidation at a partial conversion which is high enough so that the concentration of unreacted hydrocarbon is very low throughout the run, improving product quality and yields. The semi-continuous part of the oxidation is conducted so that the concentration of TMLA is low, usually about 1–5 mole percent, thus preventing premature catalyst deactivation, and the bromine concentration is zero or below 35 percent of the total bromine added. The total bromine added is about 0.5 to about 1.5 moles per mole of cobalt. Thus, the theoretical oxygen uptake is somewhere between 1 and 2.5 moles $O_2$/mole hydrocarbon, with 1.5-2 moles being preferred. Because of side reactions, the actual oxygen uptake may be slightly higher. Also, the semicontinuous oxidation may be run at a low enough temperature, usually about 120° C. to about 200° C., to allow maintenance of an oxygen concentration above 0.5 percent in the vent gas, with 2-8 percent being preferred. After all the hydrocarbon has been pumped in, the oxidation is finished batchwise after the addition of cerium. In the batchwise step, the temperature of reaction is increased from about 140° C. to about 175° C. to about 150° C. to about 250° C. to compensate for the decreasing reaction rate. In this step, all, or at least 65 percent, of the bromine used in the catalyst is added including all of the cerium.

Clearly, the species, with one of the three methyl groups oxidized (dimethylbenzoic acids), are formed first, and their concentration is highest at 15-30 minutes. The monomethyl dicarboxylic acids are also formed early, but they peak at about 45 minutes into the run. The desired product, TMLA, does not appear in significant concentrations until about 45 minutes, but it then rises rapidly to its maximum at the conclusion of the run at 79 minutes.

In all of the embodiments and processes of this invention as described above it is, for a variety of reasons, preferable to conduct the oxidation of PSC to TMLA using an atomic ratio of bromine to total catalyst metals in the range of about 0.4:1 to about 0.7:1. These ratios of bromine-to-catalyst metals are particularly effective when cerium is added only during the last or, in the case of a two-stage reaction, the second stage of the pseudocumene oxidation reaction. The use of bromine-to-metals ratios in the range of about 0.4:1 to about 0.7:1 in conjunction with adding cerium only during the second stage of the oxidation results in improved yields of TMLA, a reduction in the levels of side products and, as evidenced by lower CO and $CO_2$ levels in the reactor effluent gas, reduced burning. The ability to use lower amounts of bromine also results in a cost saving. Finally, the lower bromine levels are less corrosive to the reactor metallurgy.

The following examples illustrate the preferred embodiment of this invention. It will be understood that the example are for illustrative purposes only and do not purport to be wholly definitive with respect to the conditions and scope of the invention.

EXAMPLE 1

The oxidation of pseudocumene is accomplished by bubbling air through a hot (320° F.) mixture of pseudocumene (225 g) with 420 g of 95% acetic acid in the presence of cobalt and manganese acetates and HBr and zirconium to 320° F. The base case concentration of cobalt is 0.18 wt. %, manganese is 0.084 wt. %, Zr is 0.004 wt. %, all based on pseudocumene. Hydrogen bromide is added to equal a 0.9 molar bromine-to-metals ratio, but only 20 percent of the total bromine is added at the beginning of the oxidation. The remainder is added gradually with the so-called tail-out catalyst which also includes some manganese (0.01 wt. %) and zirconium (0.004 wt. %).

The temperature is gradually ramped from 320° F. to 400° F. over the 60 minute run, and the pressure is also ramped from about 120 psig to 280 psig over the same period. After the oxidation the reactor contents are collected and analyzed.

EXAMPLE 2

This oxidation was carried out just as in Example 1, but the manganese in the initial mix was 0.12 wt. % of pseudocumene, the cobalt was 0.20%, and the bromine was added at a level which produced a total molar bromine-to-metals ratio of 0.5. The bromine addition was staged such that 80% of the bromine was added via the tail-out catalyst just as in Example 1.

EXAMPLE 3

This oxidation was carried out just as in Example 2, but cerium was added via the tail-out catalyst to a concentration of 0.06% of pseudocumene.

EXAMPLE 4

This oxidation was identical to that of Example 3, but the cobalt concentration was 0.18 wt. %, the initial manganese was 0.16 wt. %, and the cerium in the tail-out was 0.10 wt. %.

EXAMPLE 5

This oxidation was similar to Example 4, but the cerium was added to the initial mix instead of the tail-out catalyst. The cerium was added at a level of 0.08 wt. % of pseudocumene. The initial manganese was 0.14 wt. %, and the cobalt was 0.18 wt. % of pseudocumene.

Table 1 contains the yield breakdown for each of these examples and shows the impact of reducing the bromine as well as the impact of adding cerium into the tail-out catalyst. Comparing Examples 1 and 2 shows the positive effect of increasing the manganese and lowering the bromine. However, the yield increase was only 1.3%.

When cerium was added (compare Examples 3 and 4 with Example 2) the yield increase becomes 2.0-2.2 mole %. Example 5 shows that adding the cerium to the initial catalyst eliminates the benefits.

TABLE 1

| Mole % Yield | Example 1 | Example 2 | Example 3 | Example 4 | Example 5 |
|---|---|---|---|---|---|
| Trimellitic | 90.0 | 91.3 | 92.2 | 92.4 | 89.7 |
| Intermediates | 0.9 | 0.8 | 0.6 | 0.6 | 1.4 |
| Low Boilers | 2.6 | 2.2 | 2.0 | 1.9 | 3.3 |
| High Boilers | 1.8 | 1.5 | 1.5 | 1.3 | 1.4 |
| CO + $CO_2$ | 4.7 | 4.2 | 3.7 | 3.9 | 4.2 |

I claim:

1. A process for the oxidation of pseudocumene with molecular oxygen to trimellitic acid under liquid-phase conditions in the presence of a catalyst comprising one or more heavy metal oxidation catalyst comprising cerium having a valence of plus three, zirconium, cobalt and manganese to provide from about 3 to about 10 milligram atoms total metals per gram mole of pseudocumene plus a source of bromine, at a temperature in the range of about 100° C. to about 275° C., the process comprising the staged addition of the bromine component in at least two stages wherein 0 to about 35 percent by weight of the total bromine is added in the first stage and the remainder is added in the last stage, and wherein all the cerium is added in the last stage, and wherein the temperature in the last stage is upward from about 175° C. to about 275° C., and the temperature in the preceding stage is between about 125° C. and about 165° C.

2. The process of claim 1, wherein a source of bromine is added to provide a total of about 1.4 to about 10 milligram atoms total bromine per gram mole of pseudocumene.

3. The process of claim 1, wherein the catalyst comprises one or more heavy metal oxidation catalysts comprising cerium, zirconium, cobalt, and manganese, and wherein the cerium content is about 9 to about 30 weight percent, the zirconium content is about 2 to about 5 weight percent, the manganese content is about 25 to about 40 weight percent, and the cobalt content is about 30 to about 70 weight percent, the amount of each metal present being given in weight percent of the total metals present, and wherein a source of bromine is added to provide a total weight ratio of bromine added of about 30 to about 100 weight percent of the total metal catalyst present.

4. The process of claim 1, wherein the oxidation is in an acetic acid solvent in an oxidation zone wherein the weight ratio of acetic acid to pseudocumene is in the range of about 1.0 to about 2.5:1.0, and wherein the catalyst is a cerium-cobalt-manganese-bromine catalyst to provide about 3 to about 10 milligram atoms total metals per gram mole of pseudocumene, and wherein a source of bromine is added to provide a total of about 1.4 to about 10 milligram atoms total bromine per gram mole of pseudocumene.

5. The process of claim 2, wherein the oxidation is in an acetic acid solvent in an oxidation zone wherein the weight ratio of acetic acid to pseudocumene is in the range of about 1 to about 2.5:1, and wherein the catalyst is a cerium-zirconium-cobalt-manganese-bromine catalyst, and wherein the atomic ratio of cerium to cobalt is about 1:2 to about 1:25, and wherein the atomic ratio of zirconium to cobalt is about 1:10 to about 1:100.

6. A process for the oxidation of pseudocumene with molecular oxygen is trimellitic acid under liquid-phase conditions in the presence of a catalyst comprising a source of cerium, a source of cobalt, a source of manganese, plus a source of bromine with or without a source of zirconium, at a temperature in the range of about 100° C. to about 250° C., which process comprises conducting the oxidation in a two-step process wherein the first oxidation is a semi-continuous oxidation conducted at a temperature of about 100° C. to about 200° C. so that only about one to about two methyl groups on the average on each benzene ring are converted to carboxylic acid groups, thus avoiding poisoning the catalyst and completing the oxidation of partially oxidized pseudocumene to trimellitic acid in a batch oxidation process at a temperature of from about 140° C. to about 175° C. to about 150° C. to about 250° C., and conducting the staged addition of the bromine component in at least two stages wherein 0 to about 35 percent by weight of the total bromine is added in the first stage of bromine addition and the remainder is added in the last stage of bromine addition, and wherein all the cerium is added in the last stage.

7. The process of claim 6, wherein the catalyst comprises one or more heavy metal oxidation catalysts comprising cerium, zirconium, cobalt and manganese to provide about 3 to about 10 milligram atoms total metals per gram mole of pseudocumene, and wherein a source of bromine is added to provide a total of about 1.4 to about 10 milligram atoms total bromine per gram mole of pseudocumene.

8. The process of claim 6, wherein the catalyst comprises one or more heavy metal oxidation catalysts comprising cerium, zirconium, cobalt, and manganese, and wherein the cerium content is about 9 to about 30 weight percent, the zirconium content is about 2 to about 5 weight percent, the manganese content is about 25 to about 40 weight percent, and the cobalt content is about 30 to about 70 weight percent, the amount of each metal present being given in weight percent of the total metals present, and wherein a source of bromine is added to provide a total weight ratio of bromine added of about 30 to about 100 weight percent of the total metal catalyst present.

9. The process of claim 6, wherein the oxidation is in an acetic acid solvent in an oxidation zone wherein the weight ratio of acetic acid to pseudocumene is in the range of about 1 to about 2.5:1, and wherein the catalyst is a cerium-cobalt-manganese-bromine catalyst to provide about 3 to about 10 milligram atoms total metals per gram mole of pseudocumene, and wherein a source of bromine is added to provide a total of about 1.4 to about 10 milligram atoms total bromine per gram of pseudocumene.

10. The process of claim 7, wherein the oxidation is in an acetic acid solvent in an oxidation zone wherein the weight ratio of acetic acid to pseudocumene is in the range of about 1 to about 2.5:1, and wherein the catalyst is a cerium-zirconium-cobalt-manganese-bromine catalyst, and wherein the atomic ratio of zirconium to cobalt is about 1:15 to about 1:45, and wherein the atomic ratio of cerium-to-cobalt is about 1:2 to about 1:25.

11. The process of claim 6, wherein the oxidation is conducted so that the heat of reaction is removed from the liquid phase by condensing to a liquid materials vaporized by the liquid-phase oxidation, wherein the condensate is returned to the oxidation reaction during the first 80 to about 95 percent of the oxidation reaction, and wherein the condensate is withdrawn from the oxidation during the last 5 to about 20 percent of the oxidation reaction.

12. The process of claim 11, wherein the catalyst comprises one or more heavy metal oxidation catalysts comprising cerium, zirconium, cobalt and manganese to provide about 3 to about 10 milligram atoms total metals per gram mole of pseudocumene, and wherein a source of bromine is added to provide a total of about 1.4 to about 10 milligram atoms total bromine per gram mole of pseudocumene.

13. The process of claim 11, wherein the catalyst comprises one or more heavy metal oxidation catalysts comprising cerium, zirconium, cobalt, and manganese, and wherein the cerium content is about 9 to about 30 weight percent, the zirconium content is about 2 to about 5 weight percent, the manganese content is about 25 to about 40 weight percent, and the cobalt content is about 30 to about 70 weight percent, the amount of each metal present being given in weight percent of the total metals present, and wherein a source of bromine is added to provide a total weight ratio of bromine added of about 30 to about 100 weight percent of the total metal catalyst present.

14. The process of claim 11, wherein the oxidation is in an acetic acid solvent in an oxidation zone wherein the weight ratio of acetic acid to pseudocumene is in the range of about 1 to about 2.5:1, and wherein the catalyst is a cerium-cobalt-manganese-bromine catalyst to provide about 3 to about 10 milligram atoms total metals per gram mole of pseudocumene, and wherein a source of bromine is added to provide a total of about 1.4 to about 10 milligram atoms total bromine per gram mole of pseudocumene.

15. The process of claim 12, wherein the oxidation is in an acetic acid solvent in an oxidation zone wherein the weight ratio of acetic acid to pseudocumene is in the range of about 1 to about 2.5:1 and wherein the catalyst is a cerium-zirconium-cobalt-manganese-bromine catalyst, and wherein the atomic ratio of zirconium of cobalt is about 1:15 to about 1:45, and wherein the atomic ratio of cerium to cobalt is about 1:2 to about 1.25.

16. A process for the oxidation of pseudocumene with molecular oxygen to trimellitic acid under liquid-phase conditions in the presence of a source of cerium, a source of cobalt, a source of manganese, plus a source of bromine with or without a source of zirconium, at a temperature in the range of about 100° C. to about 200° C., which process comprises conducting the oxidation of the pseudocumene so that the heat of reaction, is removed from the liquid phase by condensing to a liquid materials, vaporized by the liquid-phase oxidation wherein the condensate is returned to the oxidation reaction during the first 80 to about 95 percent of the oxidation reaction and wherein the condensate is withdrawn from the oxidation during the last 5 to about 20 percent of the oxidation reaction.

17. The process of claim 1, wherein the oxidation is a two-step process in an acetic acid solvent, and wherein the catalyst comprises one or more heavy metal oxidation catalysts comprising cerium, zirconium, cobalt and manganese to provide about 3 to about 10 milligram atoms total metals per gram mole of pseudocumene and a source of bromine, and wherein the first oxidation is a semi-continuous oxidation conducted at a temperature of about 130° C. to about 165° C. so that only about one to about two methyl groups on the average on each benzene ring are converted to carboxylic acid groups, thus avoiding poisoning the catalyst and completing the oxidation of partially oxidized pseudocumene to trimellitic acid in the presence of cerium in a batch process at a temperature of from about 175° C. to about 225° C.

18. The process of claim 1, wherein the oxidation is in an acetic acid solvent, the weight ratio of acetic acid to pseudocumene is in the range of about 1.0 to about 2.5:1.0, and wherein the catalyst is a cerium-zirconium-cobalt-manganese-bromine catalyst, and wherein the atomic ratio of cerium to cobalt is about 1:2 to about 1:25, and wherein the atomic ratio of zirconium to cobalt is about 1:15 to about 1:45.

19. The process of claim 17, wherein the weight ratio of acetic acid to pseudocumene is in the range of about 1.0 to about 2.5:1, and wherein the catalyst is a cerium-zirconium-cobalt-manganese-bromine catalyst, and wherein the atomic ratio of zirconium to cobalt is about 1:15 to about 1:45 and wherein the atomic ratio of cerium to cobalt is about 1:2 to about 1:25.

20. The process of claim 1 wherein the source of bromine is added so that the atomic ratio of total bromine to total catalyst metals is in the range of from 0.4:1 to about 0.7:1.

21. The process of claim 2 wherein the source of bromine is added so that the atomic ratio of total bromine to total metals is in the range of from about 0.4:1 to about 0.7:1.

22. The process of claim 21 wherein the oxidation is in an acetic acid solvent.

23. The process of claim 7 wherein the oxidation is in an acetic acid solvent and wherein the source of bromine is added so that the atomic ratio of total bromine to total metals is in the range of from about 0.4:1 to about 0.7:1.

24. The process of claim 11 wherein the oxidation is in an acetic acid solvent and wherein the catalyst comprises one or more heavy metal oxidation catalysts comprising cerium, zirconium, cobalt and manganese to provide about 3 to about 10 milligram atoms total metals per gram mole of pseudocumene, and wherein the source of bromine is added so that the atomic ratio of total bromine to total metals is in the range of from about 0.4:1 to about 0.7:1.

25. The process of claim 17 wherein the source of bromine is added so that the atomic ratio of total bromine to total metals is in the range of from about 0.4:1 to about 0.7:1.

26. The process of claim 1 wherein the oxidation is in an acetic acid solvent and wherein the catalyst comprises one or more heavy metal oxidation catalysts comprising cerium, cobalt and manganese, and wherein a source of bromine is added so that the atomic ratio of total bromine to total metals is in the range of from about 0.4:1 to about 0.7:1.

* * * * *

UNITED STATES PATENT OFFICE
CERTIFICATE OF CORRECTION

Patent No. 4,992,579                              Dated February 12, 1991

Inventor(s)   Wayne P. Schammel

It is certified that error appears in the above-identified patent and that said Letters Patent is hereby corrected as shown below:

Col.  Line 3     16    "xylene" should read --xylenes--

Signed and Sealed this

Twenty-first Day of July, 1992

Attest:

DOUGLAS B. COMER

Attesting Officer    Acting Commissioner of Patents and Trademarks

UNITED STATES PATENT AND TRADEMARK OFFICE
CERTIFICATE OF CORRECTION

PATENT NO.: 4,992,579

DATED: February 12, 1991

INVENTOR(S): Wayne P. Schammel

It is certified that error appears in the above-identified patent and that said Letters Patent is hereby corrected as shown below:

On the title page, Abstract, line 1 patent reads "trimelitic acid" patent should read --trimellitic acid--

| | | |
|---|---|---|
| 7 | 48-49 | "It will be understood that the example are for illustrative purposes only" should read --It will be understood that the examples are for illustrative purposes only-- |
| 9 | 40-41 | "the oxidation of pseudocumene with molecular oxygen is trimellitic acid" should read --the oxidation of pseudocumene with molecular oxygen to trimellitic acid-- |

UNITED STATES PATENT AND TRADEMARK OFFICE
CERTIFICATE OF CORRECTION

PATENT NO. : 4,992,579

DATED : February 12, 1991

INVENTOR(S) : Wayne P. Schammel

It is certified that error appears in the above-indentified patent and that said Letters Patent is hereby corrected as shown below:

Column 11, lines 12-13, "the atomic ratio of cerium to cobalt is about 1:2 to about 1.25." should read --the atomic ratio of cerium to cobalt is about 1:2 to about 1:25.--

Signed and Sealed this

Thirtieth Day of April, 1996

Attest:

BRUCE LEHMAN

Attesting Officer     Commissioner of Patents and Trademarks